(12) United States Patent
Benfey et al.

(10) Patent No.: US 7,612,252 B2
(45) Date of Patent: Nov. 3, 2009

(54) HOMEOTIC GENES AND PROTEINS, USES THEREOF

(76) Inventors: Philip Benfey, 307 Hilllsborough St., Chapel Hill, NC (US) 27514; Tal Nawy, 500 N. Duke St., Apt. 54-307, Durham, NC (US) 27701

( * ) Notice: Subject to any disclaimer, the term of this patent is extended or adjusted under 35 U.S.C. 154(b) by 428 days.

(21) Appl. No.: 10/482,605

(22) PCT Filed: Jun. 25, 2002

(86) PCT No.: PCT/US02/20251

§ 371 (c)(1),
(2), (4) Date: Sep. 9, 2004

(87) PCT Pub. No.: WO03/000862

PCT Pub. Date: Jan. 3, 2003

(65) Prior Publication Data

US 2005/0066385 A1 Mar. 24, 2005

Related U.S. Application Data

(60) Provisional application No. 60/300,648, filed on Jun. 25, 2001.

(51) Int. Cl.
*C12N 15/29* (2006.01)
*C12N 15/82* (2006.01)
(52) U.S. Cl. .................... 800/278; 536/23.2; 536/24.1
(58) Field of Classification Search ............... 800/278; 536/23.1, 23.6, 24.1; 435/320.1
See application file for complete search history.

(56) References Cited

OTHER PUBLICATIONS

Benfey et al (1990, Science 250:959-966).*
Benfey et al (1989, EMBO J, 8(8):2195-2202).*
Busch et al (1999, Science 285:585-587).*
Lohmann et al (2001, Cell 105 :793-803).*
Beven et al. (1983) Nature 304:184.
Chuang, C. et al. (2000) PNAS 97:4985-4990.
Dolan L. et al. (1993) Developement 119:71-84.
Feldman, L.J. (1976) Planta 128:207-212.
Feldman, L.J. (1976) American Journal of Botany 63:345-355.
Feldman, L.J. (1984) American Journal of Botany 71:1308-1314.
Fernandez, D.E. et al. (2000) The Plant Cell vol. 12 pp. 183-197.
Fraley et al. (1985) Biotechnology 3:629.
Herrera-Estrella et al. (1983) Nature 303:209.
Imlau, A. et al. (1999) Plant Cell 11:309-322.
Kaya, H. et al. (2001) Cell 104:131-142.
Klee et al. (1985) Bio/Technology 3:637-642.
Ma, H. et al. (1991) Genes & Development vol. 5, No. 3:484-495.
Mayer, K.F.X. et al. (1998) Cell 95:805-815.
Morrison, S.J. et al. (1997) Cell 88:287-298.
Odell et al. (1985) Nature 313:810.
Rounsley, S.D. et al. (1995) The Plant Cell vol. 7, No. 8:1259-1269.
Scheres, B. et al. (1994) Development 120:2475-2487.
Schoof, H. et al. (2000) Cell 100:635-644.
Sieburth, L.E. et al. (1997) Plant Cell 9:355-365.
Tirlapur, U.K. et al. (1999) Plant Journal 20:363-370.
Umeda, M. et al. (2000) PNAS 97:13396-13400.
van den Berg, C. et al. B. (1995) Nature 378:62-65.
van den Berg, C. et al. (1997) Nature 390:287-289.
Velten et al. (1984) Embo J. 3:2723-2730.
Velten et al. (1985) Nucleic Acid Res. 13:6981-6998.
Zhang et al. (1998) Science 279:407-409.

* cited by examiner

*Primary Examiner*—Stuart F. Baum (57) ABSTRACT

The homeotic gene AGL42 in *Arabidopsis* has been cloned and characterized and is presented herein, both alone and in association with expression control sequences and in vectors which may be used e.g. for transgenic expression. The gene exhibits the role of controlling meristem maintenance. A labeled construct is shown to serve as a marker for identity of the quiescent cells within the meristem. Both the DNA and protein are disclosed.

4 Claims, 4 Drawing Sheets

Figure 1. schematic of the *Arabidopsis* root tip

Figure 2. GUS expression in ET433 primary root tip

Figure 3. Confocal images of p*AGL42*::GFP roots counter-stained with propidium iodide.

Figure 4. Aberrant *agl42-1* root

Figure 5 agl42 nucleotide sequence
I. atggttagaggaaagatagagatgaagaaaatagaaaacgcaacgagtagacaagtgactt
tctcaaaaagaagaaatggttttgttgaagaaagcttatgagctctcagtactctgcgatgctc
aactctctctcatcatcttctcccagagaggaaggctttatgaattctctagctctga
II. tatgcagaagacgatcgaacgctaccgcaagtacacaaaagatcatgaaaccagcaatca
cgactcacaaattcacttgcag
III. caattgaaacaagaagcaagccacatgataacaaagattgaactccttgagtttcacaa
gcg
IV. gaagctattgggacaaggaattgcttcttgttctctagaagagcttcaagaaatcgatag
tcaactccaaagaagtctgggaaaggtccgagaaagaaag
V. gctcaattgttcaaggagcagttggagaaactaaaagcaaag
VI. gagaaacaattgttagaagagaacgtcaagttacatcaaaag
VII. aatgttattaatccatggagaggatcatcgactgatcagcagcaagagaaatacaaagt
tatagatttgaatttggaagttgaaactgacttattcatcggtttgccaaatagaaactgcta
g
3'UTR. taacattatataatatgtttatttatttatcatgaaatattcaaaatcattcaataa
attgtgaggtaatgatttgggata

Figure 6 agl42 protein sequence
mvrgkiemkkienatsrqvtfskrrngllkkayelsvlcdaqlsliifsqrgrlyefss
sdmqktieryrkytkdhetsnhdsqihlqqlkqeashmitkiellefhkrkllgqgias
csleelqeidsqlqrslgkvrerkaqlfkeqleklkakekqlleenvklhqknvinpwr
gsstdqqqekykvidlnlevetdlfiglpnrnc

| Sizes: | AT | %AT |
|---|---|---|
| Exon 1 -- 182 | .110 | 60% |
| Exon 2 -- 82 | 46 | 56% |
| Exon 3 -- 62 | 38 | 61% |
| Exon 4 -- 100 | 58 | 58% |
| Exon 5 -- 42 | 25 | 60% |
| Exon 6 -- 42 | 28 | 67% |
| Exon 7 -- 123 | 80 | 65% |
| 3'UTR -- 81 | 66 | 81% |

| Total cDNA | | | | Protein |
|---|---|---|---|---|
| 714 bp | 451 | 63% | (total) | 210 aa |
| 633 bp | 385 | 61% | (coding) | |

Genomic Region
3.5 kb

HOMEOTIC GENES AND PROTEINS, USES THEREOF

CROSS-REFERENCE TO RELATED APPLICATIONS

The present application is a National Stage Application claiming the priority of copending PCT Application No. PCT/US02/20251 filed Jun. 25, 2002, which in turn, claims priority from Provisional Application Ser. No. 60/300,648, filed Jun. 25, 2001. Applicants claim the benefits 35 U.S.C. §120 as to the PCT Application and priority under 35 U.S.C. §119 as to the Provisional Application, and the entire disclosures of both applications are incorporated herein by reference in their entireties.

BACKGROUND OF THE INVENTION

I The study of plant morphology and morphogenesis has developed extensively with the advent of recombinant technology. Investigators have identified individual homeotic genes that act either alone or in concert with each other to determine structures in the developing plant. Variations in plant morphology have been noted through the ages, and studies have revealed that mutations of critical homeotic genes may account for such structural aberrations. In many instances such changes may be prompted by response of the plant to environmental stress. The bulk of these investigations have sought to determine both the manner in which such aberrations result and possible avenues for application of such aberrations either to develop new plant strains and structures, or alternatively, to correct the defect caused by the mutation and to assure uniform and normal plant growth.

Figure 1:
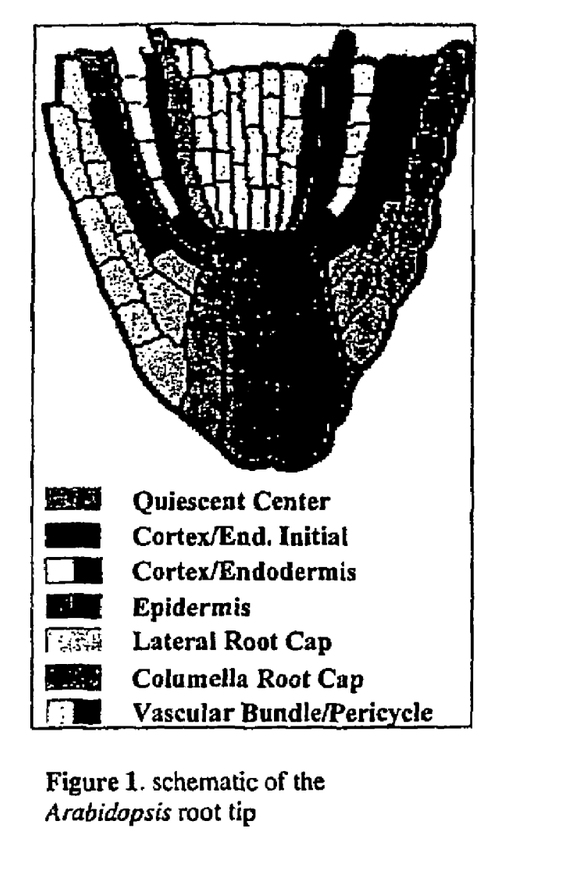
FIG. 1 schematically depicts the structure of the root tip of *Arabidopsis thaliana*.

More particularly, plants adapt to environmental stresses through altered growth patterns and physiological changes. These changes occur primarily at the tips of the plant, through the regulated division of cells in regions termed apical meristems. Meristems are first laid down in the embryo, but actively and continuously produce new organs in the germinated seedling and adult plant. The root apical meristem is a particularly suitable system for studying organogenesis because of its relatively simple organization and well characterized, predictable cell divisions (Dolan et al., 1993). Most of the root is a cylinder composed of concentric layers of four basic tissues (epidermis, ground tissue [cortex and endodermis], pericycle and vascular bundle from outside to in; FIG. 1). Anatomical studies and fate mapping trace the origin of each tissue type to a ring of cells at the root apex known as initials (Scheres et al., 1994). Initials produce two cells in every stem-cell division: the regenerated initial, and a daughter cell which differentiates as it is displaced from the initial by further rounds of division. Thus, growth in the root occurs by addition of cells at the tip. Surrounding the root apex is a set of protective cells which make up the root cap. The columella (central) root cap has its own set of initials which produce daughters downwards in the direction of the root tip. Lateral root cap shares a common initial with the epidermis. Together, the initials surround a set of approximately four central cells in *Arabidopsis* termed central cells, or the quiescent center (QC). The meristem is considered to comprise the QC, initials, and their rapidly dividing derivatives in the root tip.

The QC, at the heart of the mersitem, has been the focus of intense investigation for nearly two centuries. Early theories posited that central cells must divide rapidly to give rise to all tissues of the root (see Barlow, 1976). This idea was debunked by the English investigator Frederick Clowes, who fed $^3$H-thymidine to maize seedlings, and discovered that the population of central cells rarely enter S phase of the cell cycle (Clowes, 1961). Slow cycling time has since been described as an almost universal aspect of stem cells, which often accompanies self-renewal as a defining character (Morrison et al., 1997). Soon after the discovery of mitotic quiescence, levels of RNA and protein synthesis were determined to be very low in the QC (Clowes, 1961). Despite these properties, it was shown that occassional divisions could give rise to any cell of the root, and damaged meristems were regenerated by inducing QC proliferation (Feldman, 1976). This led Barlow to propose his Founder Cell Theory, in which QC cells were described as the ultimate source of all cells in the root (Feldman, 1984). Totipotency of QC cells was demonstrated through in vitro experiments, which proved that the QC is sufficient for regenerating an organized root in culture (Feldman & Torrey, 1976). Torrey (1972) looked beyond the role of the QC as a stem cell population by proposing a function in patterning. He argued that the QC served as a "template", by which the meristem and root was patterned. Although a quiescent center has been detected in all plant species analysed to date (including *Arabidopsis*; Dolan et al., 1993), its function remains poorly characterized.

More recent insights into QC function have come from laser ablation studies. Ablation of a single QC cell results in the differentiation of contacting initials, as evidenced by accumulation of starch in the columella initial and a premature asymmetric division in the ground tissue (van den Berg et al., 1995). Thus, the QC must be responsible for a short-range signal that prevents the differentiation of surrounding stem cells. An additional, long-range "top-down" signal for differentiation was also detected in roots by laser ablation (van den Berg, 1997). In order to maintain its undifferentiated state, the QC must be refractile to this signaling from more mature cells. Given their function in continuous organogenesis, meristems must be able to balance stem-cell maintenance with differentiation. In the shoot apical meristem, stem cells in a central zone undergo cell divisions to produce daughters in a peripheral zone where organ primordia are initiated. Balance between these processes in the shoot has recently been shown to result from an autoregulatory loop between signaling molecules (Schoof et al., 2000). The homeodomain protein WUSCHEL is expressed in an organizing region just below the central zone, and is required for maintenance of stem cell fate (Mayer et al., 1998). WUS activates transcription of CLV3, a ligand which signals the CLV1 receptor kinase in the central and peripheral zones to inhibit transcription of WUS. Thus, as stem cells leave the central zone, they lose their ability to repress WUS, an activator of stem cell fate; these cells are replenished by the activity of WUS in the central zone.

Superficial similarities between the root and shoot meristems, in combination with the results of laser ablation, hint that a similar feedback regulation may occur between the QC and surrounding cells. Along these lines, the FASCIATA1 and 2 genes have recently been shown to affect both shoot and root apical meristem organization as a double mutant (Kaya et al., 2001). FAS genes encode proteins involved in replication-fork dependent nucleosome assembly, and are thus hypothesized to maintain stable epigenetic transcriptional states in the meristems. In fas double mutants, the WUS expression domain is expanded, leading to stem cell overproliferation and stem fasciation. Candidate targets in the root are few. Recently, the root-tip specific expression of CakAt1, a CDK-activating kinase, has been shown to be necessary for preventing differentiation of initials (Umeda et al., 2000). This is likely to be a downstream player of signaling or morphogenic processes.

SUMMARY OF THE INVENTION

The present invention is predicated on the discovery that a gene named herein AGL42, a MADS box transcription factor, expresses specifically in the quiescent center and is necessary for the maintenance of meristem organization. The gene was identified by an enhancer trap strategy. DS box genes are well known for their roles in the flower, but among the root-specific MADS genes, only ANR1 has been assigned a function (in nitrate response; Zhang and Forde, 1998). This family has played key developmental roles in the plant. The availability of this new gene with remarkable expression and phenotype in the QC will finally allow for a molecular characterization of this important but enigmatic stem cell population.

Figure 5:
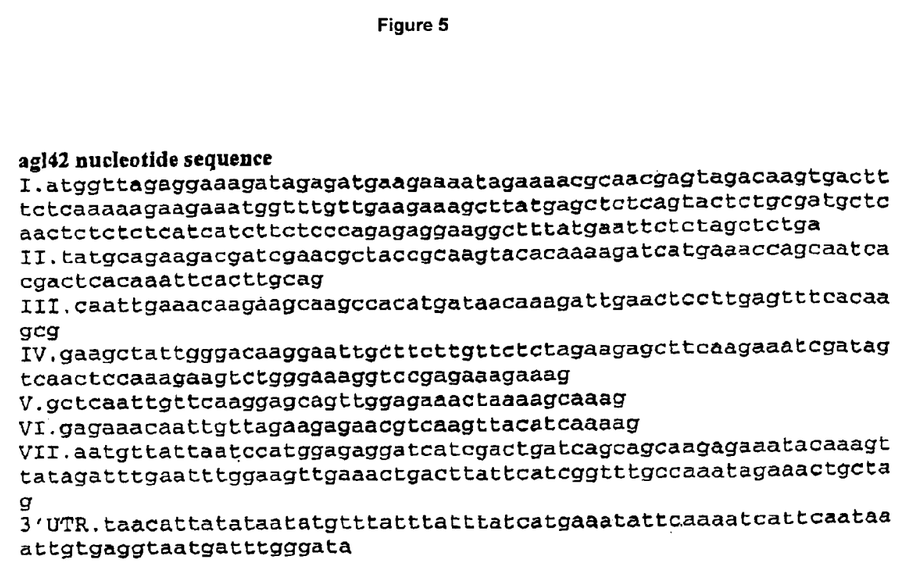
FIG. 5 presents the nucleotide sequence of AGL42 (SEQ ID NO: 1). Exons I through VII and the 3'-UTR untranslated sequence as depicted in FIG. 5 correspond to SEQ ID NOS: 3-10, respectively.

The invention also extends to the homeotic gene AGL42 in *Arabidopsis* having the DNA sequence set forth in FIG. 5. (SEQ ID NO: 1).

Figure 6:
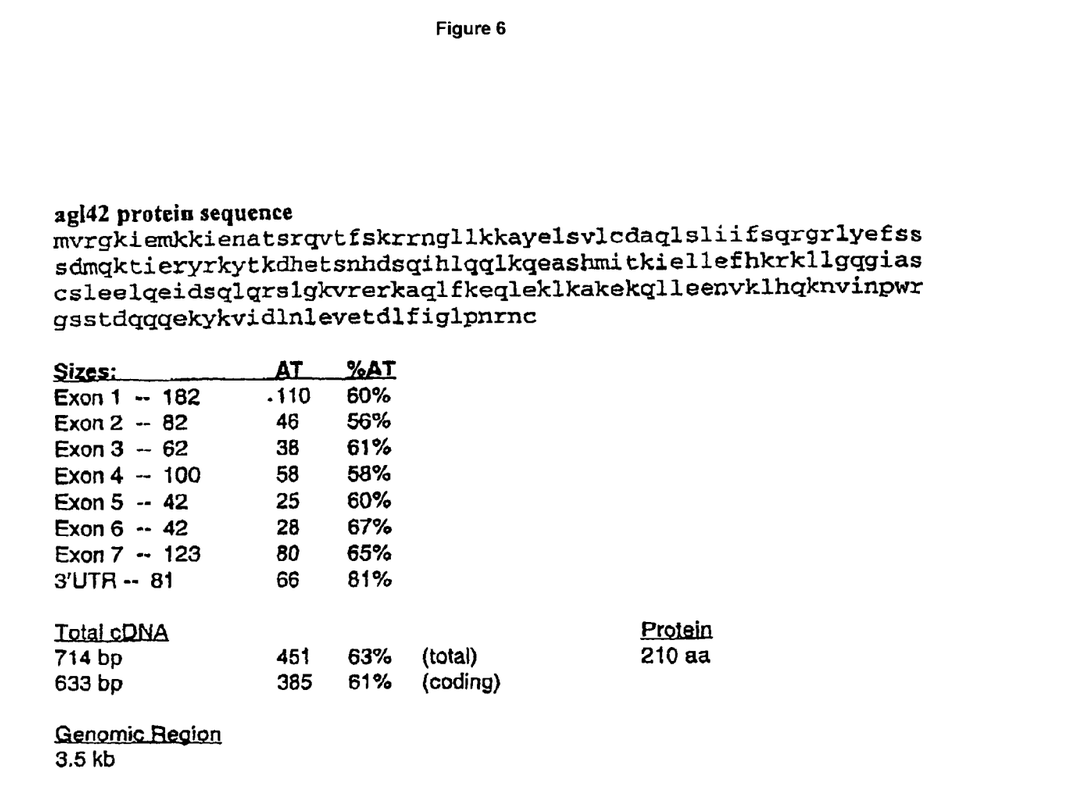
FIG. 6 presents the amino acid sequence of AGL42 (SEQ ID NO:2).

The invention extends further to DNA sequences that code the expression of the amino acid sequence set forth in FIG. 6 (SEQ ID NO:2) as well as DNA sequences that would hybridize thereto. The invention further extends to the operative linkage of said DNA sequence to an expression control sequence, including promoters such as the promoter cauliflower mosaic virus (CaMV) 35S. Naturally, other promoters such as nopaline synthetase and the rbcs E9 gene from pea are representative of other nonlimiting examples thereof. The CaMV 35S promoter is preferred as it is constitutively expressed and is particularly well-suited for the method illustrated herein.

The nucleic acid sequence of the AGL42 cDNA (SEQ ID NO: 1), presented as exons I through VII and the 3'-UTR untranslated sequence (corresponding to SEQ ID NOS: 3-10, respectively) is depicted in FIG. 5. The amino acid sequence of the AGL42 polypeptide(SEQ ID NO: 2) is depicted in FIG. 6.

In accordance with an aspect of the invention, the present gene or regulatory elements thereof may be e.g. fused to a marker such as Green Fluorescent Protein (GFP), and used to identify and monitor expression of the central cells (quiescent center) in the meristem. Such a construct was prepared in accordance herewith and its utility has been established as set forth infra.

Other objects and advantages will become apparent to those skilled in the art from a consideration of the ensuing description taken in conjunction with the following illustrative drawings.

DETAILED DESCRIPTION OF THE INVENTION

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Immobilized Cells And Enzymes" [IRL Press, (1986)]; B. Perbal, "A Practical Guide To Molecular Cloning" (1984).

The amino acid residues described herein are preferred to be in the "L" isomeric form. However, residues in the "D" isomeric form can be substituted for any L-amino acid residue, as long as the desired functional property of immuno-globulin-binding is retained by the polypeptide. NH2 refers to the free amino group present at the amino terminus of a polypeptide. COOH refers to the free carboxy group present at the carboxy terminus of a polypeptide. In keeping with standard polypeptide nomenclature, *J. BIOL. CHEM.*, 243: 3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

If appearing herein, the following terms shall have the definitions set out below.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

In accordance with the present invention and as stated earlier, a method is disclosed for the control and determination of plant organ identity, comprising the expression of one or more homeotic genes that have been determined to control the structural identity of the plant organs in question. The present invention is specifically illustrated herein with respect to the plant *Arabidopsis*, wherein the expression of the homeotic gene AGL42 results in the maintenance of the meristem region of the root, and thereby assures the continued management of stem cell maintenance and differentiation.

It is a general precept of the invention, that, while particular homeotic genes may be present and necessary for the determination of particular organ structure, it is the sufficiency of their presence that can actually control structural determination and overall plant maintenance and longevity. It is to these principles, therefore, that the present invention is directed.

The practice of the present invention is largely reliant on known techniques in molecular biology. That is, the expression of the gene in object may proceed by the preparation of the gene to include one or more promoters and the placement of the same in a suitable vector. As discussed below, the cauliflower mosaic virus (CaMV 35S promoter) may be employed to create RNA-mediated interference lines, for the purpose of preparing an allelic series of the gene. The preparation presented later on herein is illustrative and not restrictive, the scope of the invention naturally extending to other vectors, promoters and protocols suitable for use in plant transformation.

Promoters which are known or are found to cause transcription of RNA in plant cells have been described in the literature and can be used in the present invention. Such promoters may be obtained from plants or viruses and include, but are not limited to, the nopaline synthase (NOS) and octopine synthase (OCS) promoters (which are carried on tumor-inducing plasmid of *Agrobacterium tumefaciens*), the wheat histone H3 gene, the rbcs E9 gene from pea, the cauliflower mosaic virus (CaMV) 19S and $^{35}$S promoters [Odell et al., NATURE 313:810 (1985)], the light-inducible promoter from the small subunit of ribulose bisphosphate carboxylase (ssRUBISCO) as set forth in commonly assigned U.S. Pat. No. 4,990,607, and the mannopine synthase promoter [Velten et al. EMBO J. 3:2723-30 (1984); and Velten et al., NUCLEIC ACID RES. 13:6981-98 (1985)] and where desired, mixtures of one or more of the above. All of these promoters have been used to create various types of DNA constructs which have been expressed in plants, (see, e.g., PCT publication WO84/02913) (Rogers et al., Monsanto).

While the DNA sequence of the homeotic gene AGL42 or other homeotic gene of interest may be embodied in a vector such as disclosed herein in its form as sequenced, it is to be understood that, where desired, such coding sequence may be modified, to create mutants, either by random or controlled mutagenesis, using methods known to those skilled in the art. Accordingly, the invention may extend to the expression of truncated proteins and fusion proteins, as well as unmodified genes.

The 3' non-translated region contains a polyadenylation signal which functions in plants to cause the addition of polyadenylate nucleotides to the 3' end of the mRNA. Examples of suitable 3' regions are the 3' transcribed, non-translated regions containing the polyadenylated signal of genes from the T-DNA of *Agrobacterium*, the soybean storage protein genes and the small subunit of the RuBP carboxylase gene.

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNAs, from suitable eukaryotic genes, or from a synthetic gene sequence. The non-translated leader sequence can be part of the promoter sequence, or can be derived from an unrelated promoter or coding sequence as discussed above.

A DNA construct of the present invention can be inserted into the genome of a plant by any suitable method. Suitable plant transformation vectors include those derived from a Ti plasmid of *Agrobacterium tumefaciens*, such as those described by Herrera-Estrella et al. [NATURE 303:209 (1983); Bevan et al. NATURE 304:184 (1983); Klee et al. BIO/TECHNOLOGY 3:637-642 (1985); Fraley et al., BIO-TECHNOLOGY 3:629 (1985) and EPO Publication 120,516 (Schilperoort, et al.)]. In addition to plant transformation vectors derived from the Ti or root-inducing (Ri) plasmids of *Agrobacterium*, alternative methods can be used to insert the DNA constructs of this invention into plant cells. Such methods may involve, for example, the use of liposomes, electroporation, chemicals that increase free DNA uptake, transformation using viruses or pollen and the use of microprojectiles.

Choice of methodology for the regeneration step is not critical, with suitable protocols being available for hosts from Legurminosae (alfalfa, soybean, clover, etc.), Umbelliferae (carrot, celery, parsnip), Cruciferae (cabbage, radish, rapeseed, etc.), Cucurbitaceae (melons and cucumber), Gramineae (wheat, rice, corn, etc.), Solanaceae (potato, tobacco, tomato, peppers) and various floral crops. Gene expression can be altered in plants from each of the aforesaid families pursuant to the present invention.

The present invention will be better understood from a consideration of the following example which is presented for purposes of illustration and not by way of limitation. It is clear from the present disclosure, that a variety of structural modifications may be achieved by means of the principles set forth herein, and the invention is accordingly believed to extend to such diverse modifications.

EXAMPLE 1

Figure 2:
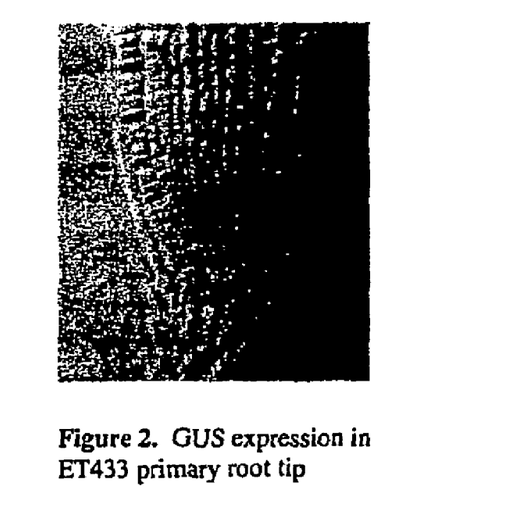
FIG. 2 is a photograph of a root tip illustrating the expression of β-glucuronidase (GUS) as part of an enhancer trap screen.

AGL42 is expressed in the root tip. As mentioned in the background, AGL42 was originally isolated in an enhancer trap screen. The screen utilized a minimal promoter driving a marker gene encoding β-glucuronidase (GUS), an enzyme that converts a colorless substrate to a blue precipitate. In the ET433 line, expression is detected in primary root tips approximately 34 days post-germination, as well as in nascent lateral root tips upon significant extension from the primary root (FIG. 2). QC cells are darkly stained, and initials of the vasculature, cortex and endodermis appear light blue. No expression is detected in other regions of the plant or in the embryo. These results elucidate two important points: first, that AGL42 has a highly specific expression pattern, suggesting that it has some function in the root meristem, and second, that AGL42 cannot be involved in processes that initially pattern the meristem in the embryo and lateral root. Thus a working hypothesis is that AGL42 is involved in meristem maintenance.

A disadvantage to using GUS is that its product has a known tendency to diffuse, particularly in certain tissues such as the vasculature. The weak staining in initials of ET433 roots may therefore represent diffusion. In addition, enhancer traps can yield artifactual expression patterns as a result of disrupted regulatory elements or position effects. RTPCR confirms that expression is limited to roots.

Figure 3:
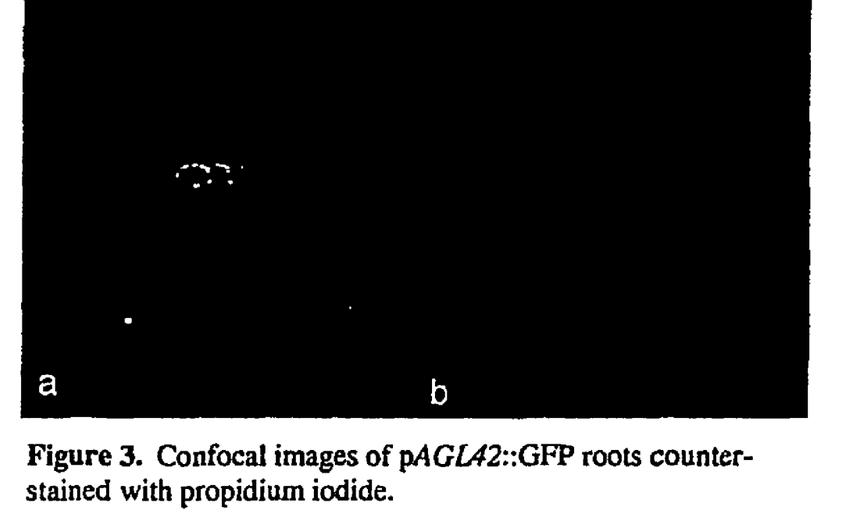
FIG. 3 is a confocal microscopic photograph showing pAGL42::GFP expression.

To verify the expression of AGL42, and to determine whether regulatory elements could be used as a tool for QC-specific expression, we have fused AGL42 regulatory sequences to Green Fluorescent Protein. The second intron in AGAMOUS, the canonical member of this gene family, is homologous to the first intron in AGL42 and has been shown to contain regulatory elements (Sieburth & Meyerowitz, 1997). To include putative regulatory sequences in the intron, we designed the construct pAGL42::GFP (deposited as ATTCC Accession No. PTA-9607) as a translational fusion including 3 kb promoter, first (MADS-box containing) exon, first intron, and part of the second exon. Temporal and spatial expression of pAGL42::GFP agrees with that of ET433 (FIG. 3a). GFP is limited to the QC cells, unless the sensitivity of the confocal microscope is increased (FIG. 3b). The weaker GFP signal in surrounding initial cells and their derivatives may be caused by low level expression in these cells, or it may be due to diffusion of the GFP molecule itself. Possible reasons for the latter include the fact that pAGL42::GFP does not contain any subcellular localization signals; plasmodesmata give cells a high connectivity in the meristem (Tirlapur & Kšnig, 1999) and GFP has been shown to move freely in this region (Imlau et al., 1999); the imaged line carries two copies of the transgene, and strength of expression appears to segregate; GFP appears to accumulate in the cytoplasm of QC cells to a level many-fold higher than in surrounding cells; and finally, older roots exhibit more of this phenomenon than roots recently initiating AGL42 expression. A version of this construct carrying ER-localized (non-diffusable) GFP should distinguish between the two possibilities.

pAGL42::GFP has proven to be a useful marker of QC identity, highlighting recent QC divisions, and allowing for a better estimate of QC composition than previously attainable.

AGL42 is a new member of the MADS box transcription factor family. Genomic DNA flanking the ET433 enhancer trap insertion was isolated, revealing a novel AGAMOUS-LIKE gene. AGL42 contains the three hallmark domains coded for by MADS box genes in plants: the highly conserved MADS DNA-binding domain and the predicted coiled-coil keratin-like (K) domain, separated by a weakly conserved short intervening (I) region. It also contains a carboxy-terminal domain that does not have a conserved function among MADS family members. In some genes it is known to serve as a transcriptional activation domain. Two splice variants were detected by RT-PCR, one of which lacks the third of three exons contributing to the K domain.

Figure 4:
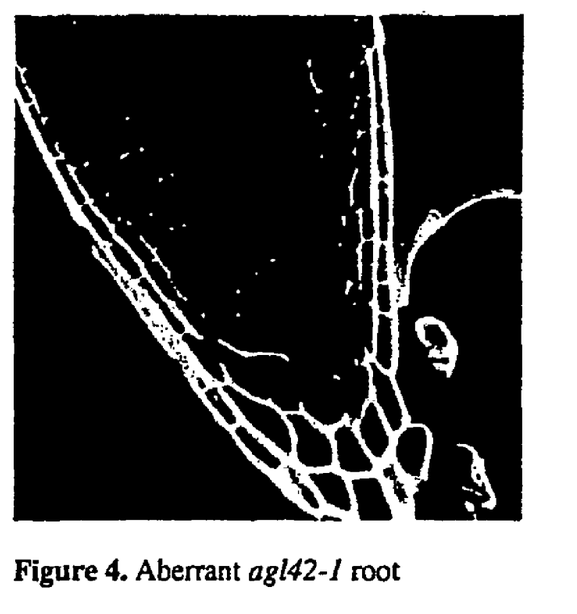
FIG. 4 is a photograph illustrating an aberrant AGL42-1 root.

AGL42 is necessary for maintenance of meristem organization. The enhancer trap line contains an 8 kb insertion in the first intron of AGL42. RT-PCR analysis reveals that some wild type transcript is produced by plants homozygous for the insertion, but weak and inconsistent amplification as compared with wild type suggests that a splicing defect results in reduced RNA levels. The low level expression of AGL42 has not been amenable to Northern analysis. Plants homozygous for the insertion (agl42-1) show no defect in growth or gross morphology when grown on plates or in soil. However, examination of root tip anatomy reveals a disorganized meristem in approximately 7% of individuals (FIG. 4). The phenotype is variable, but characterized by oblique cell division planes, displaced or missing QC cells, and cell shapes that are not observed in wild type roots. Response to various levels of sucrose and nitrogen is indistinguishable from wild type, and efforts to exacerbate the phenotype under mild heat shock have failed. An interesting discovery from this phenotype is that plants can tolerate disturbances in the usually stereotypical cellular organization without impaired root growth. Furthermore, cells in each file above an aberrant root tip are able to correct defects resulting from earlier divisions. The correction of mechanically disrupted cells in the meristem has been hypothesized to result from top-down signaling by mature cells, thus ensuring the maintenance of contiguous cell files (Scheres & Berleth, 1998). These results also discredit the "template" hypothesis of Torrey (see Background), which requires a wild type QC arrangement to pattern the rest of the root (Torrey, 1972).

A potentially confounding issue in these analyses is the variability observed in wild type roots. Under standardized growth conditions, wild type roots will occasionally give rise to mildly aberrant cell divisions in the root tip. The most common defect is in columella root cap organization. The rapidly dividing cells of the cap show a defect in up to 8% of wild type roots, so we have avoided using the root cap as an indicator of phenotype in agl42. Variation in other tissues is extremely rare and is not as severe as observed in aberrant agl42 plants.

Isolation of new agl42 alleles. To search for a null phenotype, I have used a PCR-based approach to screen a collection of over 60 000 *Arabidopsis* lines containing random insertions (Krysan et al., 1999). T2 plants have been isolated from two lines: one containing an insertion in the first intron, and another with an insertion in the fifth intron. No differences could be detected between plants harbouring an insertion in the fifth intron and wild type. Plants homozygous for the first intron insertion (agl42-2) show a similar disorganization of the root tip to agl42-1 plants, with a similar penetrance and RTPCR profile. agl42-2 plants provide an independent confirmation of the agl42-1 phenotype. The subtlety of phenotype in these lines suggest the possibility of a redundant factor in the root.

Elucidation of the true function of AGL42 requires characterizing its null phenotype. In order to obtain an allelic series of agl42, including null mutants, RNA-mediated interference lines ($^{35}$S::AGL42(RNAi)) were created. These stably transformed lines ubiquitously express AGL42 cDNA in two orientations separated by a 1 kb spacer. The primary transcript produces a double-stranded hairpin secondary structure that causes degradation of endogenous message in the plant, leading to phenotypes of varying severity (Chuang & Meyerowitz, 2000). The highly conserved MADS domain was omitted from the construct to avoid the possibility of knocking out related genes in the plant. The result of a collection of lines which are ready to analyze.

REFERENCES

Alvarez-Buylla, E. R., et al. *Plant Journal*, 24, 457-466.
Barlow, P. W. (1976) *Journal of Theoretical Biology*, 57, 433-451.
Busch, M. A., et al. (1999), *Science*, 285, 585-587.
Chuang, C. et al. *PNAS*, 97, 4985-4990.
Clowes, A. F. L. (1961) *Apical mersitems*. Blackwells Scientific, Springfield, Ill.
Deyholos, M. K. et al. (2000) *Plant Cell*, 12, 1799-810.
Dolan, L., et al. (1993) *Development*, 119, 71-84.
Drews, G. N., et al. (1991) *Cell*, 65, 991-1002.
Feldman, L. J. (1976) *Planta*, 128, 207-212.
Feldman, L. J. (1984) *American Journal of Botany*, 71, 1308-1314.
Feldman, L. J. et al (1976) *American Journal of Botany*, 63, 345-355.
Ferrándiz, C., et al. (2000) *Development*, 127, 725-734.
Honma, T. et al. (2001) *Nature*, 409, 525-529.
Imlau, A., et al. (1999) *Plant Cell*, 11, 309-322.
Kaya, H., et al. (2001) *Cell*, 104, 131-142.
Krysan, et al. (1999) *Plant Cell*, 11, 2283-2290.
Liljegren, S. J., et al. (2000) *Nature*, 404, 766-770.
Lucas, W. J., et al. (1995) *Science*, 270, 1980-1983.
Mayer, K. F. X., et al. (1998) *Cell*, 95, 805-815.
McLean, B. G., et al. (1997) *Plant Cell*, 9, 1043-1054.
Mizukami, Y. et al. (1992) *Cell*, 71, 119-131.
Morrison, S. J., et al. (1997) *Cell*, 88, 287-298.
Pelaz, S., et al. (2000) *Nature*, 405, 200-203.
Perbal, M., et al. (1996) *Development*, 122, 3433-3441.
Sabatini, S., et al. (1999) *Cell*, 99, 463-472.
Scheres, B. et al.(1998) *Current Opinion in Plant Biology*, 1, 32-36.
Scheres, B., et al. (1994) *Development*, 120, 2475-2487.
Schoof, H., et al.(2000) *Cell*, 100, 635-664.
Sessions, A., et al. (2000) *Science*, 289, 779-781.
Sieburth, L. E. et al. (1997) *Plant Cell*, 9, 355-365.
Tirlapur, U. K. et al. (1999) *Plant Journal*, 20, 363-370.
Umeda, M., et al. (2000) *PNAS*, 97, 13396-13400.
van den Berg, C., et al. B. (1995) *Nature*, 378, 62-65.
van den Berg, C., et al.(1997) *Nature*, 390, 287-289.
Walbot, V. (1985) *Trends in Genetics*, 1, 165-169.
Weigel, D. et al. (1994) *Cell*, 78, 203-209.
Zhang, H. et al. (1998) *Science*, 279, 407-409.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

---

What is claimed is:

1. The construct pAGL42::GFP having ATCC Accession No. PTA-9607.

2. A nucleic acid construct comprising AGL42 sequence fused to a marker, wherein the AGL42 sequence confers expression of the marker in the central cells or quiescent center of a plant, wherein the AGL42 sequence is comprised of upstream promoter sequence, first exon sequence, first intron sequence and second exon sequence of AGL42, and wherein the first exon sequence is as set out in SEQ ID NO: 3 and the second exon sequence is as set out in SEQ ID NO: 4 and wherein the construct is pAGL42::GFP having ATCC Accession No. PTA-9607.

3. The construct of claim 2 wherein the marker is green fluorescent protein (GFP).

4. A method of identifying and monitoring the central cells or quiescent center in a plant comprising inserting into the genome of said plant or expressing in said plant the construct pAGL42::GFP having ATCC Accession No. PTA-9607.

* * * * *

SEQUENCE LISTING

```
<160> NUMBER OF SEQ ID NOS: 2

<210> SEQ ID NO 1
<211> LENGTH: 713
<212> TYPE: DNA
<213> ORGANISM: Arabidopsis thaliana

<400> SEQUENCE: 1
atggttagag gaaagataga gatgaagaaa atagaaaacg caacgagtag acaagtgact      60
ttctcaaaag aagaaatggt ttgttgaaga aagcttatga gctctcagta ctctgcgatg     120
ctcaactctc tctcatcatc ttctcccaga gaggaaggct ttatgaattc tctagctctg     180
atatgcagaa gacgatcgaa cgctaccgca agtacacaaa agatcatgaa accagcaatc     240
acgactcaca aattcacttg cagcaattga aacaagaagc aagccacatg ataacaaaga     300
ttgaactcct tgagtttcac aagcggaagc tattgggaca aggaattgct tcttgttctc     360
tagaagagct tcaagaaatc gatagtcaac tccaaagaag tctgggaaag gtccgagaaa     420
gaaaggctca attgttcaag gagcagttgg agaaactaaa agcaaaggag aaacaattgt     480
tagaagagaa cgtcaagtta catcaaaaga atgttattaa tccatggaga ggatcatcga     540
ctgatcagca gcaagagaaa tacaaagtta tagatttgaa tttggaagtt gaaactgact     600
tattcatcgg tttgccaaat agaaactgct agtaacatta tataatatgt ttatttattt     660
atcatgaaat attcaaaatc attcaataaa ttgtgaggta atgatttggg ata             713

<210> SEQ ID NO 2
<211> LENGTH: 210
<212> TYPE: PRT
<213> ORGANISM: Arabidopsis thaliana

<400> SEQUENCE: 2
```

-continued

```
Met Val Arg Gly Lys Ile Glu Met Lys Lys Ile Glu Asn Ala Thr Ser
1               5                   10                  15

Arg Gln Val Thr Phe Ser Lys Arg Arg Asn Gly Leu Leu Lys Lys Ala
                20                  25                  30

Tyr Glu Leu Ser Val Leu Cys Asp Ala Gln Leu Ser Leu Ile Ile Phe
                35                  40                  45

Ser Gly Arg Gly Arg Leu Tyr Glu Phe Ser Ser Ser Asp Met Gln Lys
        50                  55                  60

Thr Ile Glu Arg Tyr Arg Lys Tyr Thr Lys Asp His Glu Thr Ser Asn
65                  70                  75                  80

His Asp Ser Gln Ile His Leu Gln Gln Leu Lys Gly Glu Ala Ser His
                85                  90                  95

Met Ile Thr Lys Ile Glu Leu Leu Glu Phe His Lys Arg Lys Leu Leu
                100                 105                 110

Gly Gly Gly Ile Ala Ser Cys Ser Leu Glu Glu Leu Gln Glu Ile Asp
            115                 120                 125

Ser Gln Leu Gln Arg Ser Leu Gly Lys Val Arg Glu Arg Lys Ala Gln
        130                 135                 140

Leu Phe Lys Glu Gln Leu Glu Lys Leu Lys Ala Lys Glu Lys Gln Leu
145                 150                 155                 160

Leu Glu Glu Asn Val Lys Leu His Gln Lys Asn Val Ile Asn Pro Trp
                165                 170                 175

Arg Gln Ser Ser Thr Asp Gln Gln Glu Lys Tyr Lys Val Ile Asp
                180                 185                 190

Leu Asn Leu Glu Val Glu Thr Asp Leu Phe Ile Gly Leu Pro Asn Arg
            195                 200                 205

Asn Cys
    210
```